United States Patent [19]

Hankins et al.

[11] 4,039,461

[45] Aug. 2, 1977

[54] POLYALKYLENE GLYCOL POLYALKYLENE POLYAMINE SUCCINIMIDE DISPERSANTS FOR LUBRICANT FLUIDS

[75] Inventors: Tad L. Hankins, Fullerton, Calif.; Ting-I Wang, Cherry Hill, N.J.

[73] Assignee: Atlantic Richfield Company, Philadelphia, Pa.

[21] Appl. No.: 572,026

[22] Filed: Apr. 28, 1975

Related U.S. Application Data

[60] Division of Ser. No. 368,678, June 11, 1973, Pat. No. 3,897,454, and a continuation-in-part of Ser. No. 765,959, Oct. 8, 1968, abandoned.

[51] Int. Cl.² ............................................. C10M 1/32
[52] U.S. Cl. ............................................. 252/51.5 A
[58] Field of Search ................................... 252/51.5 A

[56] References Cited

U.S. PATENT DOCUMENTS

| | | | |
|---|---|---|---|
| 3,184,474 | 5/1965 | Catto et al. | 252/51.5 A X |
| 3,525,693 | 8/1970 | Lyle et al. | 252/51.5 A X |
| 3,632,511 | 1/1972 | Liao | 252/51.5 A |
| 3,746,645 | 7/1973 | Saito et al. | 252/51.5 A |
| 3,897,454 | 7/1975 | Hankins et al. | 252/51.5 A X |

OTHER PUBLICATIONS

Kalichevsky et al., "Petroleum Refining with Chemicals", 1956 Elsevier Publ. Co., pp. 583–612.

*Primary Examiner*—Delbert E. Gantz
*Assistant Examiner*—Andrew H. Metz
*Attorney, Agent, or Firm*—John B. Goodman; Frank J. Uxa

[57] ABSTRACT

A new class of dispersant compounds and compositions and a series of novel lubricant compositions are disclosed. Polyalkylene glycol succinimides which may be derived from maleic acids and anhydrides are useful as dispersants in, for example, polyglycol base fluids. Lubricating compositions including such dispersant compositions are also described.

11 Claims, No Drawings

POLYALKYLENE GLYCOL POLYALKYLENE POLYAMINE SUCCINIMIDE DISPERSANTS FOR LUBRICANT FLUIDS

This is a division of application Ser. No. 368,678 filed June 11, 1977, now U.S. Pat. No. 3,897,454.

This application is a continuation-in-part of application, Ser. No. 765,959 filed Oct. 8, 1968, now abandoned.

The present invention relates to chemical compositions and, more particularly, to chemical compositions useful as lubricating fluid additives and to lubricating fluid compositions. Still more particularly, this invention relates to polyalkylene glycol succinimide lubricant additives and methods for making same.

Motor fuel lubricants, such as conventional automobile motor oil or oils designed for special applications, e.g., marine, aircraft and stationary engines, conventionally include oxidation inhibitors and dispersant additives. Viscosity improvers, etc., are also conventionally added to the basic lubricant fluid to provide particular characteristics desired in the end lubricating composition.

Many hydrocarbon-based or hydrocarbon-containing additives are commercially available for use in conventional hydrocarbon lubricating fluids. It is, of course, desirable that any successful additive be soluble in the lubricating fluid at all potential operating or handling conditions. Long chain aliphatic hydrocarbon substituted succinic acid-amine derivatives have been proposed as dispersant additives for hydrocarbon-based lubricant fluids, see U.S. Pat. No. 3,172,892, for example.

A new class of potentially commercially valuable base lubricating fluids has been developed, however, in which most known dispersant additives are insoluble or have only limited solubility. An example of this new type of lubricant are products commonly referred to as polyglycols, e.g., polypropylene glycol diether polymers. Therefore, it would be advantageous to provide improved dispersant additives for such lubricant fluids.

Accordingly, an object of the present invention is to provide an improved lubricant for use, for example, as crankcase oils and as lubricants generally, which comprise polyglycols, such as polypropylene glycol diether polymer, as a base fluid and an improved sludge dispersant additive.

A further object of the present invention is to provide an improved dispersant additive comprising polyalkylene glycol succinimides.

An additional object of the present invention is to provide a method for producing improved dispersant additives for use, for example, in polyglycol lubricant fluids. Other objects and advantages of the present invention will become apparent hereinafter.

A new class of compounds, termed polyalkylene glycol succinimides, useful as a dispersant additive in lubricant fluids, e.g., polyglycols, has now been discovered. These compounds are selected from the group consisting of

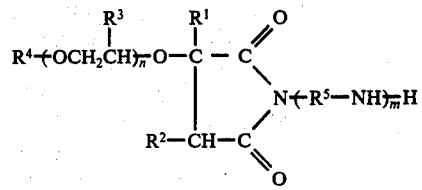

and mixtures thereof, wherein each $R^1$ and $R^2$ is independently selected from the group consisting of hydrogen and monovalent hydrocarbonaceous radicals containing less than about 10 carbon atoms, each $R^3$ and $R^4$ is independently selected from the group consisting of hydrogen and alkyl containing from 1 to about 10, preferably from 1 to about 4, carbon atoms, each $R^5$ is independently selected from the group consisting of divalent hydrocarbonaceous radicals containing from 1 to about 3 carbon atoms, $n$ is a positive integer in the range from about 1 to about 100, preferably from about 10 to about 100, and $m$ is a positive integer from about 1 to about 10. Preferably, $n$ is at least 3 times $m$, and more preferably $n$ is from about 5 to about 15 times $m$.

The present dispersant additive compositions are useful as dispersants in lubricating compositions for use, for example, in automobile engines, aircraft engines, marine engines, stationary engines and the like. These lubricating compositions may comprise a major amount of a base fluid of lubricating viscosity, such as polyglycols which have the following generalized structural formula:

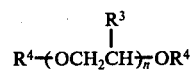

wherein $R^3$, $R^4$ and $n$ are as described previously. In a preferred embodiment, $R^3$ is methyl and each $R^4$ is independently selected from the group consisting of alkyl containing from 1 to about 4 carbon atoms, more preferably, methyl. In this preferred embodiment, the base fluid is termed a polypropylene glycol diether polymer. These base fluids are commercially available and may have viscosities ranging from about 50 SUS to about 2000 SUS, preferably from about 100 SUS to about 1000 SUS, at 100° F. The viscosity index of these base fluids may range from about 30 to about 220, preferably from about 80 to about 200.

The present dispersant additive concentration level may be from about 0.1 percent to about 10 percent, preferably from about 1 percent to about 5 percent, by weight of the total lubricating composition. Conventional oxidation inhibitors may also be added, in an amount sufficient to inhibit the oxidation of the base fluid, for example, in the range from about 0.1 percent to about 5 percent, preferably in the range from about 0.5 percent to about 3 percent, by weight of the total lubricating composition. Many conventional oxidation inhibitors have been found to be successful, for example, 4,4-methylene, bis-2, 6-ditertiary butyl phenol, alkylated phenols, phenyl alphanaphthylamine, and alkylated diphenylamines were found to be successful oxidation inhibiting additives.

The dispersant compositions of the present invention may be obtained by contacting polyalkylene glycol polymer, described hereinafter, with a maleic compound in the amount of from about 0.1 to about 3, preferably from about 0.5 to about 1.5, moles of glycol polymer per mole of maleic compound at conditions sufficient to etherify at least a portion of the maleic compound at the carbon-carbon double bond. This etherified product is contacted with a polyalkylene polyamine in the amount of from about 0.1 to about 3, preferably from about 0.5 to about 1.5, moles of polyamine per mole of maleic compound contacted above at conditions sufficient to react at least a portion of the etherified product with the amine to form the present dispersant compositions.

As noted above, a polyalkylene glycol polymer is contacted with the maleic compound at conditions sufficient to etherify at least a portion of the maleic compound at the carbon-carbon double bond. These contacting conditions are not critical to the present invention and may vary over a broad range depending, for example, on the chemical structure of the materials being contacted, the degree of etherification desired and the like variables. Preferably, this contacting takes place at conditions such that both the polyalkylene glycol ether and maleic compound are substantially in the liquid phase. Thus, the contacting pressure is preferably maintained at a level so that a substantial portion of the polyalkylene glycol polmer, maleic compound, etherified product and solvent, if any, is in the liquid phase. Typical contacting pressures range from about 0.1 atmosphere to about 50 atmospheres or more, preferably from about 1 atmosphere to about 10 atmospheres. Contacting temperatures in the range from about 25° C. to about 250° C., preferably from about 150° C. to about 225° C., may be utilized. This contacting may be carried out for a period of time from about 1 hour to about 500 hours, preferably from about 10 hours to about 200 hours.

The etherified product prepared, for example, as described above, is contacted with a polyalkylene polyamine under conditions to form the dispersant compositions of the present invention. The conditions at which this contacting occurs are not critical to the present invention and may vary over a broad range. Preferably, this contacting occurs in the liquid phase and, therefore, contacting pressure is preferably maintained so that a substantial amount of the etherified product, polyalkylene polyamine dispersant composition and solvent, if any, is in the liquid phase, for example, in the range from about 0.1 atmospheres to about 50 atmospheres or more, preferably in the range from about 1 atmosphere to about 10 atmospheres. Typical contacting temperatures range from about 50° C. to about 300° C., preferably from about 100° C. to about 225° C. This contacting may be carried out for a period of time, for example, in the range from about 1 hour to about 100 hours, preferably from about 10 hours to about 50 hours.

In certain instances, it may be advantageous to carry out either one or both of the above-described contactings in the presence of an inert solvent, i.e., a solvent which will not materially adversely affect the formation of the etherified product or the dispersant compositions of the present invention. Examples of suitable solvents include paraffinic, cycloparaffinic and aromatic hydrocarbons containing up to about 10 or more carbon atoms per molecule, such as hexane, cyclohexane, octane, benzene, toluene, xylenes and the like. More than one solvent may be used and different solvents may be used for each of the two contactings. When a solvent is used, it is preferred that the solvent comprise at least about 20%, more preferably at least about 30%, by weight of the total liquid material present during the contacting. The solvent may be removed from either the etherified product or the present dispersant compositions by conventional procedures, e.g., simple or vacuum distillation and the like.

The polyalkylene glycol polymer suitable for use in producing the dispersant compositions of the present invention may be selected from the group consisting of

and mixtures thereof, wherein each $R^3$ and $R^4$ are independently selected from the group consisting of hydrogen and alkyl containing from 1 to about 10, preferably from 1 to about 4, carbon atoms; and $n$ is a positive integer in the range from about 1 to about 100, preferably from about 10 to about 100. Typical examples of the alkyl groups from which $R^3$ and $R^4$ may be selected include methyl, ethyl, propyl, butyl, hexyl, nonyl, decyl and the like. More preferably, $R^3$ and $R^4$ are all methyl groups and $n$ is in the range from about 10 to about 40.

The maleic compound from which the present additives may be derived are selected from the group consisting of

and mixtures thereof, wherein $R^1$ and $R^2$ are independently selected from the group consisting of hydrogen and monovalent hydrocarbonaceous radicals containing less than about 10 carbon atoms. Typical examples of the monovalent hydrocarbonaceous radicals from which $R^1$ and $R^2$ may be chosen include alkyl, such as methyl, ethyl, propyl, butyl, pentyl, hexyl, nonyl, and the like; alkenyl such as ethenyl, propenyl, butenyl, hexenyl, nonenyl, and the like; aryl, alkaryl, and alkenaryl such as phenyl, methyl phenyl, ethyl phenyl, ethenyl phenyl, propyl phenyl, propenyl phenyl and the like; aralkyl and aralkenyl, such as phenyl methyl, phenyl ethyl, phenyl ethenyl, phenyl propyl, phenyl propenyl and the like. Preferably, $R^1$ and $R^2$ are selected from the group consisting of hydrogen and alkyl containing from 1 to about 6 carbon atoms. More preferably, $R^1$ and $R^2$ are both hydrogen.

The polyalkylene polyamines from which the present additives may be derived are selected from the group consisting of

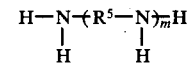

and mixtures thereof, wherein each $R^5$ is independently selected from the group consisting of divalent hydrocarbonaceous radicals containing from 1 to about 3 carbon atoms; and $m$ is a positive integer from 1 to about 10. Typical examples of the divalent hydrocarbonaceous radicals from which each $R^5$ may be independently selected include methylene, ethylene, ethenylene, propylene, propenylene, and the like. It is preferred that all $R^5$'s be the same. More preferably, all $R^6$'s are selected from the group consisting of ethylene and propylene, in particular, ethylene.

The above-described hydrocarbonaceous radicals may include non-hydrocarbonaceous substituents. Suitable substituents include those which do not materially interfere with the effectiveness, e.g., dispersant properties, of the compositions of the present invention. Typical examples of such non-interferring substituents include OH, $NH_2$, and the like radicals. Also, the definitions of all the radicals, e.g., $R^1$ through $R^5$, and the positive integers, e.g., $m$ and $n$, given in detail for the reactants, e.g., polyalkylene glycol polmers, maleic compound and polyalkylene polyamine, apply to the corresponding radicals and positive integers described previously in the dispersant compositions of the present invention.

The following examples illustrate more clearly the process of the present invention. However, these illustrations are not to be interpreted as specific limitations on the invention.

EXAMPLE I

The following example illustrates certain of the advantages of the present invention.

0.1 mole of a polypropylene glycol polymer having the following approximate structure:

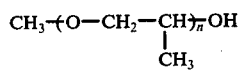

wherein n is a positive integer averaging about 25 and 0.1 mole of maleic anhydride were added to a 500 ml. reaction flask equipped with a water-cooled condenser, along with 100 ml. of xylene. The mixture was heated to 80° C., then cooled to 74° C. After 24 hours, the temperature was increased to reflux. After 68 hours at reflux, the temperature was 155° C., after 116 hours the temperature was 172° C., and after 164 hours the temperature was 201° C. At this point, the reaction flask was cooled down.

0.08 mole of triethylenetetramine and 50 mls. of toluene were added to the reaction flask and the mixture was heated to reflux. After 46 hours the temperature was 157° C. Moisture coming off from the mixture was collected as the color of the mixture turned to a dark brown. After about 52 hours, the product was vacuum treated at 150° C. and 7 mm. Hg. for 4 hours to remove the solvent prior to solubility testing and evaluation for dispersant effectiveness. Infrared analysis and molecular weight determination confirmed the presence of compounds containing both the ether and amide linkages characteristic of the present compounds.

The product of the above processing was blended with a commercially available end-blocked polypropylene glycol diether polymer so that this product amounted to 5 percent by weight of the total composition. The commercially available end-blocked polypropylene glycol diether polymer nominally has a viscosity of 58.3 SUS at 210° F., 201 SUS at 100° F., a viscosity index of 161, a pour point of −50° F., a flash point of 520° F. and a fire point of 565° F. The compounded composition was clear with no observable cloudiness or separation. A commercially available oxidation inhibitor was added at a 3 percent level. The resulting composition is useful as an engine lubricant.

Dispersant effectiveness was tested by blending the product of the above processing with a sample of the commercially available end-blocked polypropylene glycol ether described above which had been used in engines used in dynamometer tests. The blend was mixed in a Waring Blender for 5 minutes. The resulting sample was observed for sludge separation. Paper chromatographic spot tests were also used to determine dispersant effectiveness. Data showing the relative effectiveness of the dispersant composition of this invention are given in Table I along with comparative data using other known and experimental dispersant additives.

TABLE I

DISPERSANT TESTS
WARING BLENDER, HIGH SPEED - 5 MINUTES

| Code Number | % Conc. | Structure | Hrs.Settling 24 % Separation | 240 % Separation |
|---|---|---|---|---|
| Standard #1 | 100 | Used Lubricant from chassis dynamometer test on Chevrolet | 19 | 72 |
| Standard #2 | 100 | Used Lubricant from chassis dynamometer test on Ford | 4 | 58 |
| 649-37-5 | 5 | Product of maleic anhydride, polypropylene glycol polymer and triethylenetetramine comprising** $$CH_3\!-\!(OCH_2CH)_n\!-\!O\!-\!\overset{CH_3}{\underset{\vert}{C}}\!-\!\overset{H}{\underset{\vert}{C}}\!-\!\overset{O}{\underset{}{C}}\diagdown_{N-(CH_2CH_2NH)_3H} / H\!-\!C\!-\!C\diagdown \overset{}{\underset{H}{\phantom{x}}} \overset{}{\underset{O}{\phantom{x}}}$$ wherein n is a positive integer averaging about 25. | 0 | 2 |
| 649-31-6 | 5 | $$C_{12}H_{23}\!-\!\underset{\underset{CH_2CO_2H}{\vert}}{CH}CO_2\overset{CH_3}{\underset{\vert}{C}}HCH_2\!-\!(O\overset{CH_3}{\underset{\vert}{C}}HCH_2)_n\!OR$$ | 4 | 43 |
| 649-36-1 | 5 | Tetrapropenylsuccinic anhydride plus triethylenetetramine | 3 | 19* |
| 649-31-7 | 5 | $$C_{12}H_{23}\!-\!\underset{\underset{CH_2CO-(NHCH_2CH_2)_3NH_2}{\vert}}{CH}CO_2\overset{CH_3}{\underset{\vert}{C}}HCH_2\!-\!(O\overset{CH_3}{\underset{\vert}{C}}HCH_2)_n\!OR$$ | 3 at 72 | 8* |

TABLE I-continued
DISPERSANT TESTS
WARING BLENDER, HIGH SPEED - 5 MINUTES

| Code Number | % Conc. | Structure | Hrs. Settling 24 % Separation | Hrs. Settling 240 % Separation |
|---|---|---|---|---|
| 649-21-1 | 5 | $C_{12}H_{23}$—CHCO$\diagdown$<br>$\quad\quad\quad\quad\quad\quad\quad$ NCH$_2$CH$_2$CH$_2$NHCH$_2$CH$_2$CH$_2$NH$_2$<br>CH$_2$CO$\diagup$ | 17 | 30* |
| 649-14-1 | 5 | $C_{12}H_{23}$—CHCO$\diagdown$<br>$\quad\quad\quad\quad\quad\quad\quad$ NCH$_2$CH$_2$NHCH$_2$CH$_2$NH$_2$<br>CH$_2$CO$\diagup$<br>$\quad\quad\quad\quad\quad\quad$ +<br>$C_{12}H_{23}$—CHCO$\diagdown$ $\quad\quad\quad\quad$ CO—CH$_2$<br>$\quad\quad\quad\quad\quad\quad\quad$ NCH$_2$CH$_2$NHCH$_2$CH$_2$N<br>CH$_2$CO$\diagup$ $\quad\quad\quad\quad\quad\quad$ CO—CH—$C_{12}H_{23}$ | 6 at 72 | 16* |
| 649-19-1 | 5 | $C_{12}H_{23}$—CHCO$\diagdown$<br>$\quad\quad\quad\quad\quad\quad\quad$ NCH$_2$CH$_2$NH$_2$<br>CH$_2$CO$\diagup$ | 3 | 58* |

*Soap like deposit formed on graduate.
**Infrared analysis and molecular weight determination indicated the presence of the compound described below by structure. However, other unidentified products are also present which, based on the improved results obtained using the compositions of the present invention, also act as dispersants.

The significant advantages of the compositions of this invention compared with other dispersants are immediately apparent. The significantly greater effectiveness of a present dispersant composition, as compared with structurally similar compounds, is quite unexpected.

EXAMPLE II

The following examples further illustrate the present invention.

0.1 mole of the polypropylene glycol polymer used in Example I and 0.2 moles of maleic anhydride along with 100 ml. of toluene are placed in a stainless steel autoclave equipped with a mechanical stirrer and temperature control means. Nitrogen is used to pressure the autoclave to 100 psi. Means are provided so that the pressure in the autoclave is maintained at 100 psi. The mechanical stirrer is activated and the temperature of the mixture in the autoclave is slowly increased to 175° C. and is maintained there for 20 hours. At this point the mixture is cooled. 0.1 mole of diethylenetriamine is added to the mixture in the autoclave and the temperature is again slowly raised to 125° C. This temperature is maintained for 15 hours after which time the mixture is cooled. Residual toluene is stripped from the mixture. Infrared analysis and molecular weight determinations confirm the presence in the stripped mixture of compounds containing both ether and amide linkages characteristic of the compounds of the present invention. The stripped mixture is tested and found to be useful as a dispersant additive in various lubricating compositions.

EXAMPLE III

Example II is repeated except that maleic acid is used in place of maleic anhydride. Infrared analysis and molecular weight determinations of the autoclave mixture after toluene stripping confirm the presence of the characteristic compounds of the present invention. This stripped autoclave mixture is found to have utility as a dispersant additive in various lubricating compositions.

EXAMPLE IV

Example II is repeated except that 0.3 mole of polypropylene glycol polymer and 0.2 mole of diethylenetriamine are used. Also, toluene is not employed as a solvent. The final autoclave mixture is analyzed as noted previously and found to contain compounds containing both ether and amide linkages characteristic of the compounds of the present invention. This autoclave mixture is tested and found to have utility as a dispersant additive.

It is difficult to overestimate the importance of providing the proper blend of lubricating fluid, dispersant composition and oxidation inhibitor. To illustrate, using a base fluid, e.g., a polyalkylene glycol diether polymer, the dispersant compositions of the present invention and an oxidation inhibitor, there is provided a potential lifetime engine lubricant. The lubricating properties of the base fluid are not significantly diminished under normal operating conditions. However, over long periods of time, the base fluid may be oxidized to form volatile components which are discharged from the engine crankcase. An effective oxidation inhibitor may, therefore, be necessary to prevent too rapid decomposition of the base fluid resulting in the necessity for continual addition or replacement of lubricant. Sludge is formed in every internal combustion engine from combustion products, wear products, etc. It is essential that this sludge be maintained in the lubricant and carried to an effective filter. Therefore, an effective dispersant composition additive is required to provide an essentially homogeneous circulating lubricant in which the sludge forming materials are maintained in dispersion. As the homogeneous lubricant is circulated through the oil filter, the sludge components are removed and the clean lubricating fluid is returned to the crankcase. Except for occasional addition of lubricating fluid, no additional attention need be given to a vehicle's engine lubricating system. The convenience and economy of this type of fluid are immediately apparent.

The lubricating compositions of this invention, the dispersant compositions, and the process for preparing these products have been set forth in rather specific terms to aid those skilled in the art to understand and to practice the invention. Departures from the specific disclosure will be made by those skilled in the art based upon the principles and teachings herein and such variations may be made without departing from the spirit and scope of the invention, as defined in the following claims.

The embodiments of the invention in which an exclusive property or privilege is claimed are defined as follows:

1. A homogeneous lubricating composition comprising a major amount of a base fluid comprising polypropylene glycol diether polymer of lubricating viscosity and a minor amount sufficient to improve the dispersant properties of said lubricating compositions of at least one compound having the following structure:

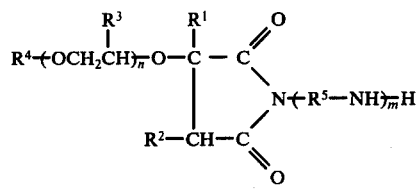

wherein each $R^1$ and $R^2$ is independently selected from the group consisting of hydrogen and monovalent hydrocarbonaceous radicals containing less than about 10 carbon atoms, each $R^3$ and $R^4$ is independently selected from the group consisting of hydrogen and alkyl containing from 1 to about 10 carbon atoms, each $R^5$ is independently selected from the group consisting of divalent hydrocarbonaceous radicals containing from 1 to about 3 carbon atoms, $n$ is a positive integer in the range from about 1 to about 100 and $m$ is a positive integer from about 1 to about 10.

2. The lubricating composition of claim 1 wherein said base fluid is selected from the group consisting of

and mixtures thereof.

3. The lubricating composition of claim 2 wherein each $R^1$ and $R^2$ is independently selected from the group consisting of hydrogen and alkyl containing from 1 to about 6 carbon atoms, each $R^3$ and $R^4$ is independently selected from the group consisting of hydrogen and alkyl containing from 1 to about 4 carbon atoms, all $R^5$'s are the same and selected from the group consisting of ethylene and propylene, $n$ is from about 10 to about 100, and $n$ is at least about 3 times $m$.

4. The lubricating composition of claim 3 wherein $R^1$ and $R^2$ are both hydrogen, all $R^3$'s and $R^4$'s are methyl, and all $R^5$'s are ethylene.

5. The composition of claim 4 wherein said lubricating composition further comprises an effective amount of at least one oxidation inhibitor which inhibits oxidation of said base fluid.

6. A homogeneous lubricating composition comprising a major amount of a base fluid comprising polypropylene glycol diether polymer of lubricating viscosity and a minor amount sufficient to improve the dispersant properties of said lubricating composition of a dispersant composition prepared by a method which comprises:

1. contacting a polyalkylene glycol polymer with a maleic compound in an amount of from about 0.1 mole to about 3 moles of glycol polymer per mole of maleic compound at conditions sufficient to etherify at least a portion of said maleic compound at the carbon-carbon double bond, said polyalkylene glycol polymer being selected from the group consisting of

and mixtures thereof, wherein each $R^3$ and $R^4$ is independently selected from the group consisting of hydrogen and alkyl containing from 1 to about 10 carbon atoms and $n$ is a positive integer from 1 to about 100, said maleic compound being selected from the group consisting of

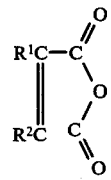 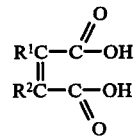

and mixtures thereof, wherein $R^1$ and $R^2$ are independently selected from the group consisting of hydrogen and monovalent hydrocarbonaceous radicals containing less than about 10 carbon atoms; and 2. contacting said etherified product with a polyalkylene polyamine in an amount from about 0.1 mole to about 3 mole of polyamine per mole of maleic compound contacted in step (1) at conditions sufficient to react at least a portion of said etherified product with said polyamine to form said dispersant composition, said polyalkylene polyamine being selected from the group consisting of

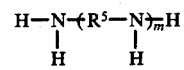

and mixtures thereof, wherein each $R^5$ is independently selected from the group consisting of divalent hydrocarbonaceous radicals containing from 1 to about 3 carbon atoms, and $m$ is a positive integer from 1 to about 10.

7. The lubricating composition of claim 6 wherein said base fluid is selected from the group consisting of

and mixtures thereof.

8. The lubricating composition of claim 7 wherein the contacting of step (1) takes place at pressures in the range from about 0.1 atmosphere to about 50 atmospheres and temperatures in the range from about 25° C. to about 250° C. for a period of time from about 1 hour to about 500 hours, and the contacting of step (2) takes place at pressures in the range from about 0.1 atmosphere to about 50 atmospheres and at temperatures in the range from about 50° C. to about 300° C. for a period of time from about 1 hour to about 100 hours.

9. The lubricating composition of claim 8 wherein $R^1$ and $R^2$ are independently selected from the group consisting of hydrogen and alkyl containing from 1 to about 6 carbon atoms, each $R^3$ and $R^4$ is selected from the group consisting of hydrogen and alkyl containing from 1 to about 4 carbon atoms, $n$ is from about 10 to about 100, all $R^5$'s are the same and $n$ is at least about 3 times $m$.

10. The lubricating composition of claim 9 wherein from about 0.5 mole to about 1.5 moles of glycol polymer is present per mole of maleic compound and from about 0.5 mole to about 1.5 moles of polyamine is present per mole of maleic compound contacted in step (1).

11. The lubricating composition of claim 10 wherein said lubricating composition further comprises an effective amount of at least one oxidation inhibitor which inhibits oxidation of said base fluid.

* * * * *